United States Patent [19]
Audette

[11] Patent Number: 6,096,050
[45] Date of Patent: Aug. 1, 2000

[54] METHOD AND APPARATUS FOR CORRELATING A BODY WITH AN IMAGE OF THE BODY

[75] Inventor: Michel Albert Audette, Montreal, Canada

[73] Assignee: Surgical Navigation Specialist Inc., Mississauga, Canada

[21] Appl. No.: 09/272,250

[22] Filed: Mar. 19, 1999

Related U.S. Application Data

[63] Continuation of application No. PCT/CA97/00693, Sep. 19, 1997.

[51] Int. Cl.[7] .................................................. A61B 5/055
[52] U.S. Cl. ...................................... 606/130; 128/653.1
[58] Field of Search ........................ 606/130; 128/653.1, 128/665, 653.2; 364/413.13; 324/318, 305, 309

[56] References Cited

U.S. PATENT DOCUMENTS 5,389,101   2/1995   Heilbrun et al. .

FOREIGN PATENT DOCUMENTS 9611624   4/1996   WIPO .

OTHER PUBLICATIONS

FIORE PD: "Image Registration Using Both Distance And Angle Information", Proceedings Of The International Conference On Image Processing, Washington, Oct. 23–26, 1995, vol. 3, pp. 220–223.

H.H. Chen and T.S. Huang, "Maximal Matching of 3–D Points For Multiple Object Motion Estimation", Pattern Recognition, vol. 21, No. 2, 1988.

Patrick J. Flynn: "3–D Object recognition with symmetric models: symmetry extraction and encoding", IEEE Transactions On Pattern Analysis And Machine Intelligence; vol. 16, No. 88, Aug. 1994, pp. 814–818.

Martial Hebert et al.: "A Spherical Representation For Recognition Of Free–Form Surfaces", IEEE Transactions On Pattern Analysis And Machine Intelligence, vol. 17, No. 7, Jul. 1995, pp. 681–690.

*Primary Examiner*—Michael Buiz
*Assistant Examiner*—William Lewis
*Attorney, Agent, or Firm*—John Orange; Orange Chari Pilla

[57] ABSTRACT

The present invention provides a system and process for correlating points on a spatial body to corresponding points on a database body formed from pre-aquired images of the spatial body. The system and process involve matching the spatial points with the corresponding database points using relative positional information between the spatial points and the database points. Symmetric false matches are detected and discarded by fitting the spatial points and database points to a first and second closed body, respectively, and comparing the orientation of the spatial points and the database points projected onto the closed bodies. In a preferred embodiment, the orientations of the spatial points and database points are compared by calculating, with respect to a matched spatial point, the longitudinal coordinates of the spatial points neighbouring the matched spatial point and calculating, with respect to the matched database point, the longitudinal coordinates of the database points neighbouring the matched database point, and comparing the difference in longitude between the points. If the difference in longitude of the spatial points corresponds to the difference in longitude of the database points, the match of the matched spatial point to the matched database point will be validated. Otherwise, the match will be considered a symmetric false match and discarded. Once at least three spatial points have been matched to corresponding database points, and the matches have been confirmed not to be false matches, a registration procedure is performed registering the spatial body to the database body by calculating a transformation mapping using the three matched pairs.

5 Claims, 11 Drawing Sheets

METHOD AND APPARATUS FOR CORRELATING A BODY WITH AN IMAGE OF THE BODY

This application is a continuation of PCT/CA97/0693 filed Sep. 19, 1997.

FIELD OF THE INVENTION

The invention relates generally to correlating a plurality of points on a spatial body with the corresponding points on a data-base body comprising previously acquired images of the spatial body. More specifically, the invention relates to a method and apparatus for correlating points on an anatomical body with images of the anatomical body stored in a data-base so that the movement of a probe, or other device, relative to the anatomical body may be displayed on the images stored in the data-base. In particular, the present invention relates to a method and apparatus for more simply performing a registration procedure between coordinates of an anatomical body and coordinates of the images stored in a data-base.

BACKGROUND OF THE INVENTION

It is known in the art for a surgeon to utilize slice images of a patient's internal organs to plan a course of a medical procedure, be it diagnostic, therapeutic or surgical. The slice images are typically generated by Computerized Tomography (CT) or by Magnetic Resonance Imaging (MRI). Images may also be captured using Angiography, Single-Photon Emission Computed Tomography, and Positron Emission Tomography methods.

The images are typically stored and displayed in a series of static images on film. In addition, the images may be stored in a computer data-base and organized pursuant to a three dimensional coordinate system, which may be referred to as image space, such that each point in each of the images is identified by a unique coordinate.

The images can be used during the medical procedure to guide instruments or probes within the body of a patient. This means that smaller incisions into the body of the patient may be made during the procedure thereby decreasing the risk for the patient and the duration of the patient's hospital stay.

However, to effectively use the images during a procedure on the patient it is necessary to display the relative position and movement of the instruments and probes being used on the patient during the procedure with respect to the images contained in the data-base. In order to display the instruments and probes on the images, it is necessary to map or correlate the spatial position of the patient relative to the images stored in the data-base. This process of mapping the anatomical body of the patient with respect to the images is referred to as "registration".

Generally speaking, the registration procedure produces a one to one mapping between coordinates of the patient space and the corresponding coordinates of the image space. In this way, by knowing the coordinates of a feature in the patient space, the corresponding coordinates in the image space can be easily determined and the features can be displayed. Once this is accomplished, the position and movement of instruments and probes relative to the patient in the patient space can be displayed relative to the images in the image space.

The first step in the registration procedure is to identify at least three points, and preferably more, on the patient and then find the corresponding points in the images. Once these points in patient and image space have been correctly matched, it is possible to determine a rigid-body transformation to map the points in patient space onto the points in image space.

In the past, in order to perform this registration procedure, it had been necessary to manually correlate points on the patient with corresponding points in the images. This has been often done by identifying points on the patient in the patient space with a probe and, immediately thereafter, identifying the corresponding point in the image space. Another manner this had been done was by identifying points in a pre-determined order in the image space and then identifying the corresponding points on the patient in the same pre-determined order. In other words, the prior art devices required the user to manually correlate a set of points in the patient space with the corresponding points in the image space in order to perform the registration procedure.

The prior art has suffered from several disadvantages. In particular, it is inefficient and time consuming for a surgeon to identify specific points on a patient in a specific order and then locate and identify the corresponding points in the image. The difficulty is compounded when the number of points increases. Furthermore, an error in entering the points cannot be quickly identified and may require the recommencement of the registration procedure.

Accordingly, there has been a need in the art for an efficient and robust automated method and system to correlate points on an anatomical body with corresponding points in the image data-base so that a registration procedure can be performed. In addition, there is a need for a system which can accept points on the anatomical body and independently correlate the points with the selected points in the image data-base, regardless of the order or number of points on the anatomical body or data-base being selected.

Moreover, in order to accomplish this task, there is a need to overcome the inherent difficulty of correlating points on a spatial body with points on an image body when the points on both bodies are symmetrical about a plane, such as a plane centred down the face of a patient In other words, there is a need for a method and system which can discriminate between a true or correct match and a mirror image or symmetrically false match between points on the image and on the patient.

SUMMARY OF THE INVENTION

Accordingly, it is an object of this invention to at least partially overcome the disadvantages of the prior art. Also, it is an object of this invention to provide an improved process and system for easily correlating points on a spatial body with the corresponding points on an image body, even though the points may be symmetrical about a plane or surface. It is also an object of this invention to provide an improved type of system and method in which any number of points in the spatial body may be entered in any order, and the system could still perform the registration procedure. It is also an object of this invention to be able to cope with additional points which may have been entered but for which no match or correlation exists.

Accordingly, in one of its aspects, this invention resides in providing a process for identifying points on a spatial body which correspond to points on a data-base body comprising previously acquired images of the spatial body, comprising the steps of: (a) selecting at least four data-base points on the data-base body; (b) determining relative positional information between the data-base points; (c) selecting at least four spatial points on the spatial body; (d) determining relative positional information between the spatial points; (e) matching a first spatial point to a corresponding data-base point by determining which of the spatial points have relative positional information which correspond to the relative positional information between the data-base points; (f) testing the first matched spatial point to determine if the first matched spatial point is a symmetric false match of the corresponding data-base point.

In a further aspect the present invention provides a system for visualizing regions of a spatial body in relation to a probe employing a data-base body of previously acquired images of the spatial body, said system comprising: (a) a probe for selecting at least four spatial points on the spatial body; (b) spatial determinator means for determining a spatial position of the probe and of the at least four spatial points; (c) data-base storage means for storing the previously acquired images of the spatial body; (d) data-base point selecting means for selecting at least four data-base points on the data-base body and determining a data-base position of the data-base points; (e) correlating means for receiving the spatial position of the spatial points and the data-base position of the data-base points and correlating the spatial points with the data-base points, said correlating means comprising: (i) matching means for matching the spatial points with the data-base points by determining relative positional information between the data-base points and determining relative positional information between the spatial points and matching a matched spatial point with a corresponding data-base point if the relative positional information of the matched spatial point corresponds to the relative positional information of the corresponding data-base point; (ii) symmetric false testing means for determining if one or more of the matched spatial points is a symmetric false match of the corresponding data-base point; (f) registering means for registering the spatial body to the data-base body based on at least three matched spatial points and the corresponding data-base points which are not symmetric false matches; and (g) displaying means for displaying a portion the data-base body corresponding to the region of the spatial body adjacent the probe.

Further aspects of the invention will become apparent upon reading the following detailed description and the drawings which illustrate the invention and preferred embodiments of the invention.

BRIEF DESCRIPTION OF THE DRAWINGS

In the drawings, which illustrate embodiments of the invention.

DETAILED DESCRIPTION OF THE PREFERRED EMBODIMENTS

Figure 1:
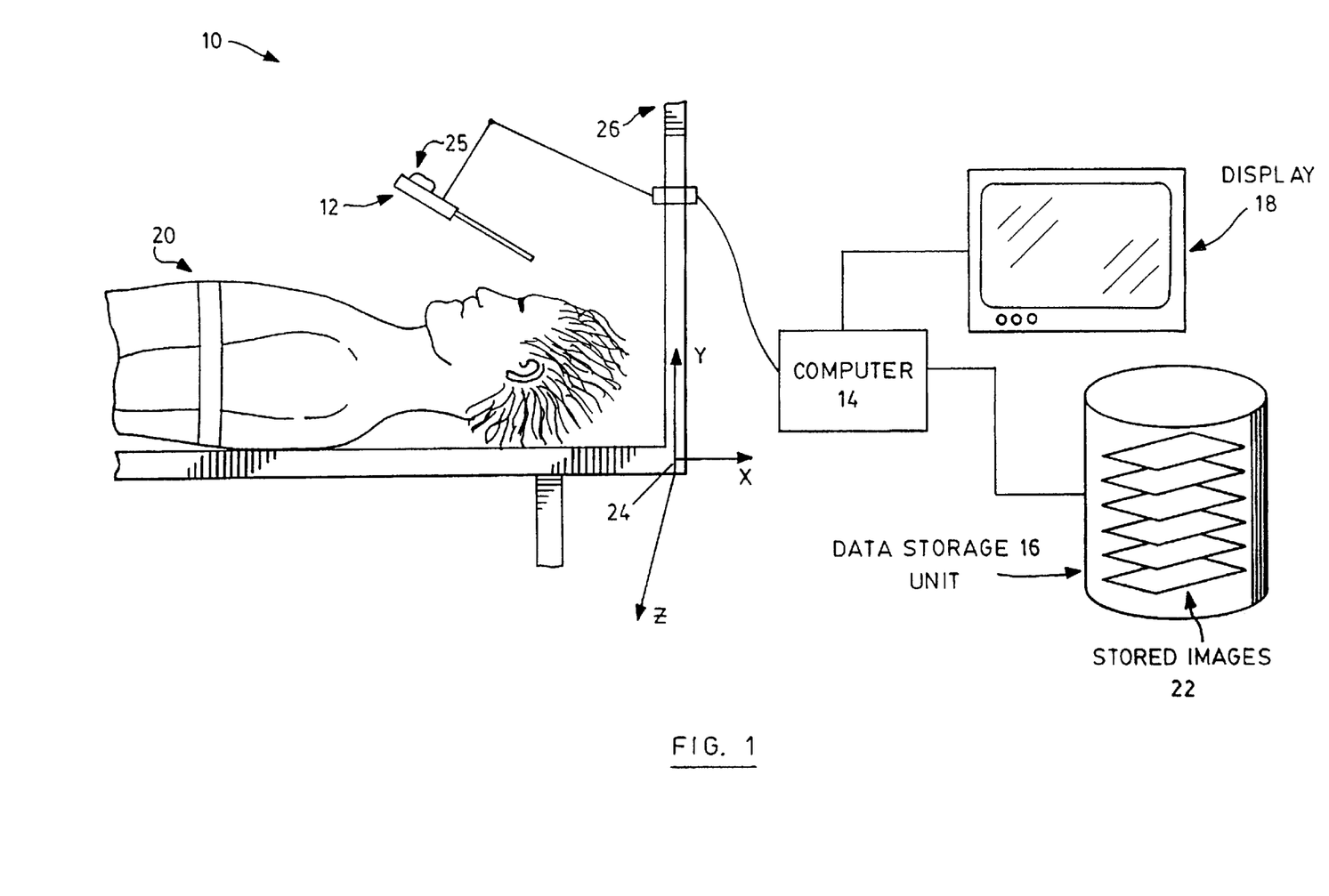
FIG. 1 shows a system according to one embodiment of the present invention.

Referring to FIG. 1, a probe-correlated system is shown generally as 10. The system has a probe 12, a computer 14, a data storage unit 16, and a display 18. The system 10 is employed, in one embodiment, to view the anatomical structure of a patient 20 on the display 18 which corresponds to the anatomical structure of the patient 20 in close proximity to the probe 12.

The computer 14 has ready access to the data storage unit 16. The data storage unit 16 contains previously acquired and digitally stored images 22 of the patient 20. These images 22 can be acquired through various medical-imaging techniques, such as Computerized Tomography, Single-Photon Emission Computed Tomography, Positron Emission Tomography, Magnetic Resonance Imaging, Ultrasound, Angiography, Magnetic Source Imaging and Magnetic Encephalography.

In addition to the images 22, the storage unit 16 stores the relative positional information regarding where each image 22 was taken with respect to each other image 22 and a common reference. In this way, a "data-base body" can be created based on the images 22 and the positional information stored in the storage unit 16. The images 22 are arranged pursuant to a three dimensional coordinate system which uniquely defines each point in the images 22. This three dimensional coordinate system shall be generally referred to as the "image space".

The digital images 22 stored in the data storage unit 16 include images 22 captured directly by medical-imaging techniques and pre-processed digital images 22 created from the captured images 22. For example, the digital images 22 together with their relative positional relationship can be pre-processed to represent the various organ surfaces of the patient in three dimensions. There are known systems, not shown, which can read the digital images 22 and generate preprocessed digital images corresponding to regions of homogeneous characteristics relating to the anatomical structure of the patient 20. In this way the "data-base body" can be represented in three dimensions in a manner showing the anatomical structure of the patient 20.

The probe 12, or any other object or instrument, is used by a surgeon or operator (not shown) to point to a particular location on the anatomical body of the patient 20. The operator can move the probe 12 around or within the anatomical body of the patient 20.

Each point in and around the patient 20 is defined by a three dimensional spatial coordinate system in the patients frame of reference. This spatial coordinate system is generally referred to as the "patient space" and has a reference point or origin which may either be on the patient or on some stable platform nearby.

In FIG. 1, the patient space has an origin 24 at the base of the stand 26 which supports the probe 12. The origin 24 has been arbitrarily selected to be in this position, and any other reference point could be used in the patient space as the origin 24.

Three axes are shown radiating from the origin 24 and these axes represent the x, y and z co-ordinates in the patient space. Each point in the patient space, and in particular each point on the patient 20, has a unique x, y and z co-ordinate in the patient space. It is understood that any type of co-ordinate system, including a spherical co-ordinate system, could be used, and, that the invention is not limited to use of an x y z co-ordinate system.

The spatial position, and if desired the spatial orientation of the probe 12 relative to the origin 24, can be determined and conveyed to the computer 14. There are a number of alternate methods which can be used to obtain the spatial coordinates of the probe 12 relative to the origin 24.

Apparatuses which can perform this function are generally referred to as spatial determinators and are known in the art.

For example, a spatial determinator (shown generally in FIG. 1 by reference numeral 25) which may be used in the system 10 comprises an electro-magnetic emitter positioned at the origin 24 and a sensor located on the probe 12. By comparing the timing and phase of transmitted signals from the emitter to received signals picked up by the sensor, the position and orientation of the probe relative to the origin 24 can be determined. A probe using this known locating method is commercially available.

Given the spatial relationship between the origin 24 and the patient 20, the computer 14 can determine the position of the probe 12 relative to the patient 20 in patient space. As the probe 12 is moved around the patient 20 it is desirable to have images displayed on the display. 20 which correspond to the anatomical features of the patient 20 near the tip of the probe 12. To display the stored images or pre-processed images 22 which correctly correspond to the region of the anatomical body of the patient 20 near the probe 12, the system 10 must be able to map positions in and around the anatomical body of the patient 20 to locations in the data-base body. In this sense, mapping is a procedure for determining the current spatial position of the probe 12 relative to the patient 20 in patient space and determining the corresponding location of the probe with respect to the data-base body. This correspondence may be determined through a procedure which maps the patient 20 or patient space to the data-base body 32 or image space. This procedure is known as "registration" since its purpose is to register or determine the correspondence between the anatomical body of the patient 20 and the data-base body 32 of the computer 14.

The registration procedure is generally as follows. A plurality of points, at least three in number, are selected on the patient 20. The images 22 are then taken and the coordinates of the points corresponding to these features are determined in image space. The spatial position or coordinates in patient space for these same features are then determined, for example by use of the probe 12 and the spatial determinator 25.

Once a number of points have been selected in both the patient space and the image space, and these points have been correlated, it is then relatively simple for the computer 14 to perform a three dimensional transformation, so that the spatial position of the patient 20 and the probe 12 in patient space are registered onto the corresponding location on the data-base body 32. Using a set of at least three, and preferably about six, points a proper and unique transformation function can be calculated which maps the spatial position of the probe 12 to the corresponding data-base body 32 location and orientation. The accuracy of this transformation function is improved by the use of a larger number of points and a statistical error minimizing technique, such as the least mean square error method.

Once the anatomical body of the patient 20 has been registered with the computer 14, the operator can move the probe in and around the patient 20, and at the same time view the hidden anatomical features of the patient 20 as they appear in the data-base body 32. The anatomical features of the patient 20 in the data-base body 32 are presented on the display 18 in relationship to the spatial position, and if desired orientation, of the probe 12.

A number of methods are known to select features on the patient 20. For example, one method involves selecting easily identifiable features of the patient 20, such as the space between the teeth, the nose or the corners of the eyes, and then using the probe 12 to register with the computer 14 the spatial position of these easily identifiable features on the patient 20 with respect to the origin 24. A preferred method involves placing small markers of a contrast material, such as a capsule filled with a copper sulphate solution for MRI on anatomical features of the patient 20, such as the forehead or back of the head. These markers can comprise the selected points on the patient 20 and the same points will appear on the images 22 and can be easily identified.

After points have been selected on the patient 20 and on the images 22 and the coordinates of the selected points in patient space and image space have been entered on the computer 14, the next step is to identify and correlate the points on the patient 20 with the points on the images 22. In the past, it has been common to manually identify and correlate the points in the image space which correspond to the points in the patient space. This was done, for example, by entering a point in the patient space and then immediately manually identifying the corresponding point in the image space. Another manner was to enter or identify the points in the patient space and the image space in the same order. This ordering information would then be used to identify and correlate the points.

By means of the method and system of the present invention, it is possible to identify and automatically correlate points in the patient space and the image space regardless of the order in which these points are identified or entered into the computer 14, and regardless of the number of points which are identified and entered in the image space or the patient space. In this regard, reference is made to FIG. 2 which shows a representation of a data-base body 32 in image space. It is understood that this representation is formed from the stored images 22 in the storage unit 16 as described above. The image space has an image origin 30 which is similar to the spatial origin 24 in patient space. In addition, dark dots marked on the data-base body 32 represent the selected data-base points 34 on the data-base body 32.

Figure 2:
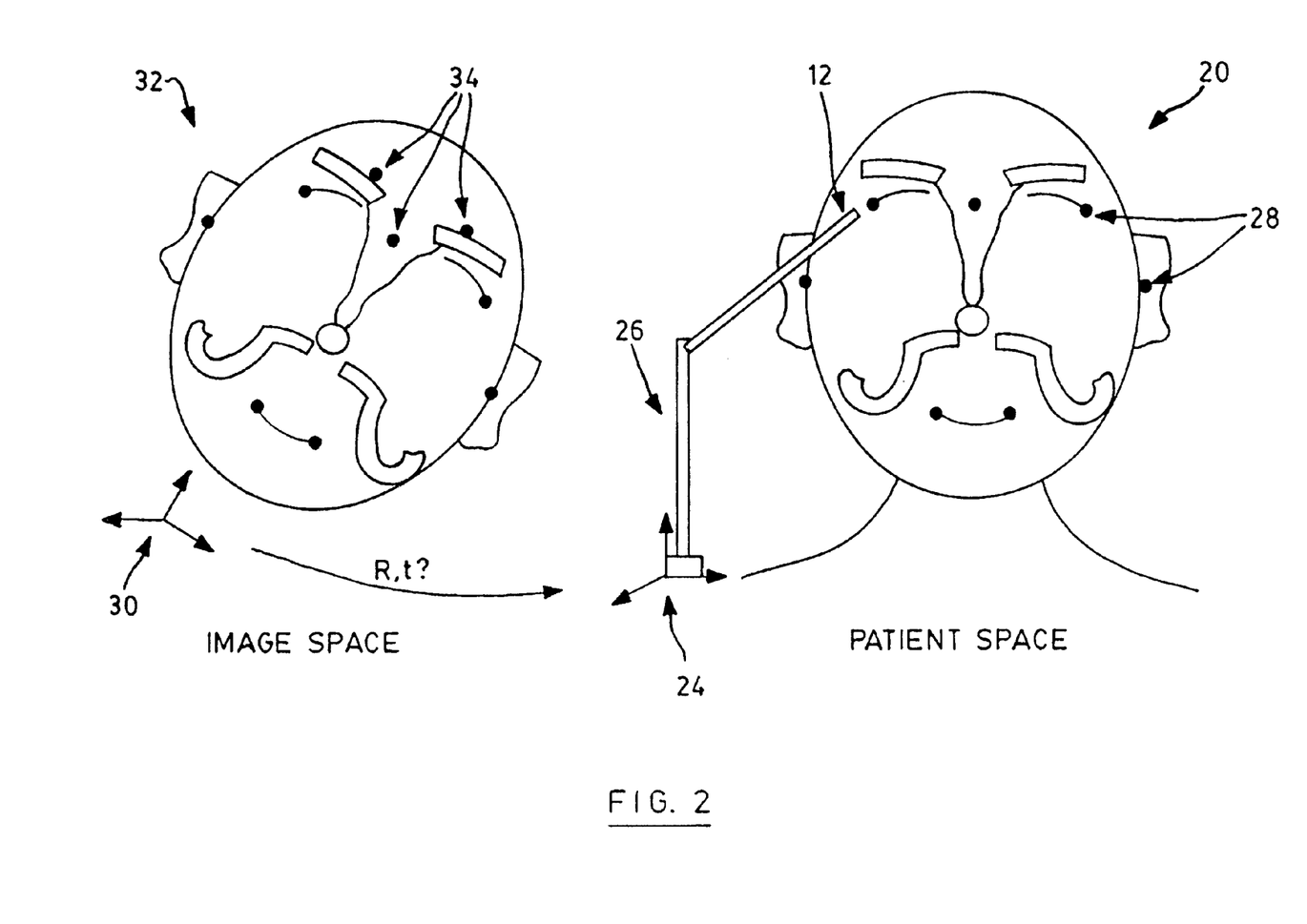
FIG. 2 shows a representation of a data-base body in image space and the patient in patient space.

FIG. 2 also shows the corresponding representation of the body in patient space, namely the patient 20, which is also shown in FIG. 1. Both FIGS. 1 and 2 show the probe 12 supported by a stand 26 with the spatial origin 24 in patient space at the base of the stand 26. In addition, several dark dots are shown on the patient 20 in patient space representing the selected spatial points 28 on the patient 20.

It is understood that the spatial points 28 may be selected in any order. Likewise, the data-base points 34 can be selected in any order. It is understood that the spatial points 28 may be selected first or the data-base points 34 be selected first, or the points can be selected in a mixed order. In either case, selection of the points 28, 34 involves identifying the point by entering the coordinates of the points 28, 34 into the computer 14.

It is necessary that at least four data-base points 34 and at least four spatial points 28 are selected, so that the following calculations may be easily made. Preferably, more than four data-base points 34 and spatial points 28 are selected to improve the chances that at least some, and preferably more than three, of the spatial points 28 match with corresponding data-base points 34.

The mapping transformation from the image space to the patient space is shown generally by the arrow pointing from the image space origin 30 to the patient space origin 24. The letters "R t" represent the rotation and translation components of the transformation. This is the mapping function the registration procedure determines.

As stated above, because there is not an equal number of data-base points 34 and spatial points 28, and because these points are not entered in any particular order, it is necessary to correlate the points in the image space with the corresponding points in the patient space. Also, it is apparent that not all of the spatial points 28 will be matched with a data-base point 34, and vice-versa.

Once spatial points 28 and data-base points 34 have been selected, the next step is to match the spatial points 28 to the data-base points 34. The first step to matching the points is determining relative positional information between each of the data-base points 34 and determining relative positional information between each of the spatial points 28. For example, in FIG. 3, the relative distance between the currently considered data-base point 34A marked with an "X" and all its neighbouring points in image space, such as point 34B, is calculated and likewise the relative distance between the currently considered spatial points 28A marked with an "X" and all its neighbours in patient space, such as 28B, is calculated. This information can be used as a first indication as to whether or not point 28A matches with data-base point 34A.

Figure 3:
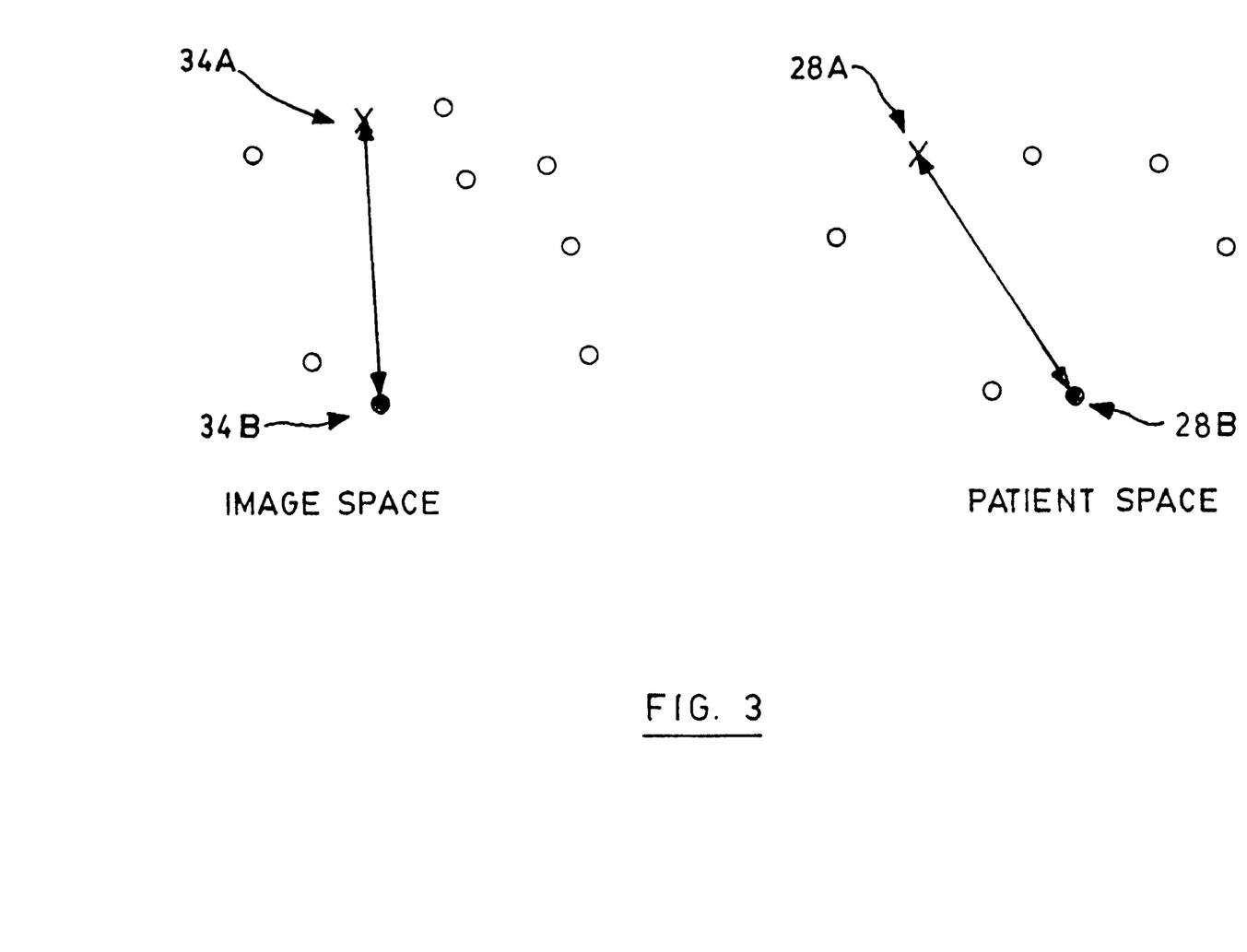
FIG. 3 shows one embodiment of the present invention where relative distances are used to match points.

The term "neighbour" refers to each of the other points in the respective space, other than the point being considered. Even though specific reference is made to neighbouring points 28B and 34B, it is understood that the calculations will be made for each of the neighbours in the respective spaces. Furthermore it is understood that this distance calculation, as well as the other position and calculations discussed below, will be performed for each combination of data-base points 34 in image space and spatial points 28 in patient space. This means that each data-base point 34 in image space will be successively considered as point 34 A was considered above with respect to its neighbours, namely the other points in image space. Likewise, each spatial point 28 will be successively considered. The best matches between the data-base points 34 and the spatial points 28 will be determined based on this information.

Figure 4:
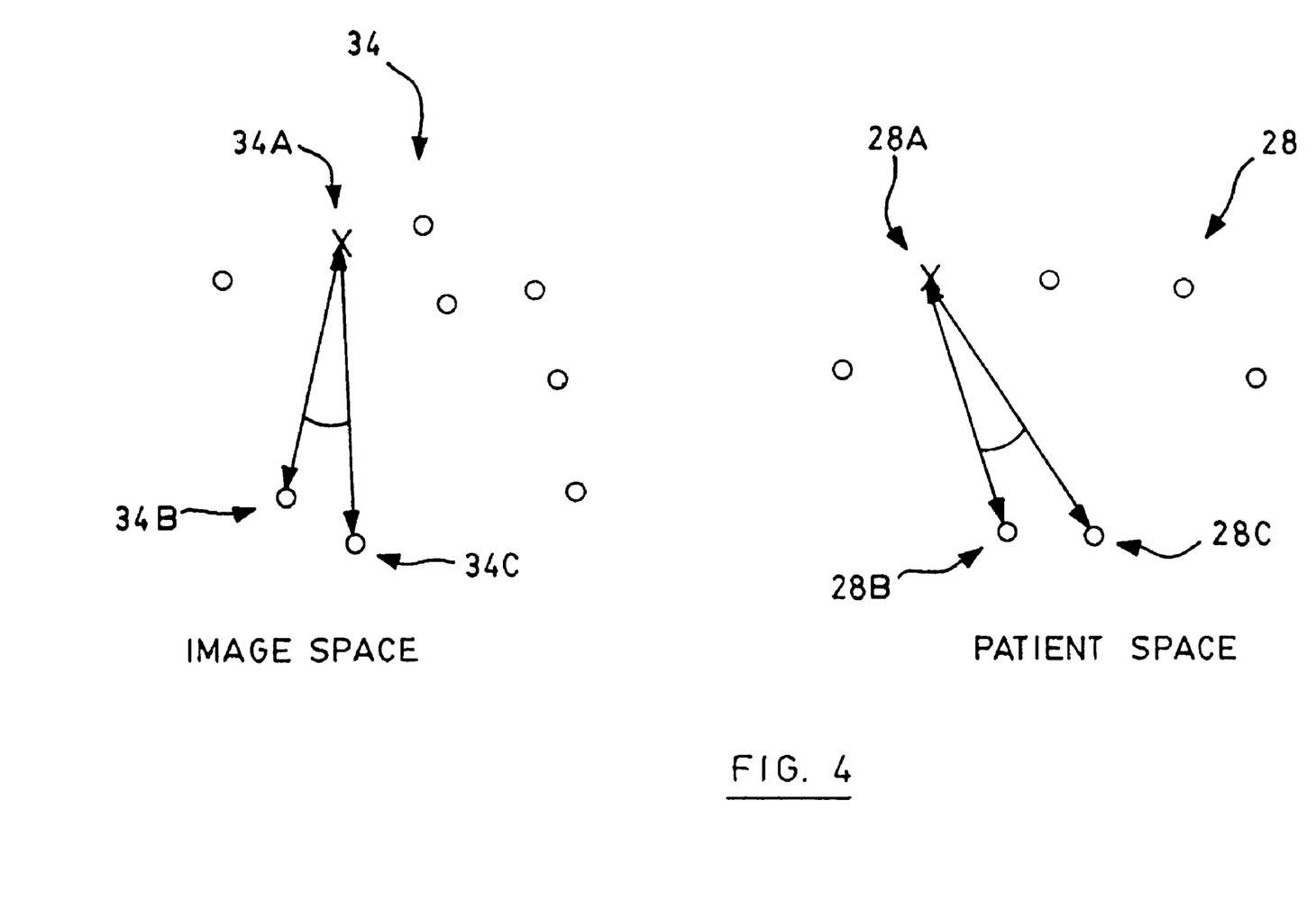
FIG. 4 shows another embodiment of the present invention where relative distances and angles between groups of three points are used to match points.

In addition to the relative distance between each of the data-base points 34 and each of the spatial points 28, other relative positional information could also be used to obtain a better match between the spatial points 28 and the data-base points 34. For example, as shown in FIG. 4, in addition to determining the relative distance between two points, the relative distance between one spatial point 28A and two other spatial points 28B, 28C, as well as the angle between that one spatial point 28A and the two other spatial points 28B, 28C can be determined. Likewise, the same relative positional information can be determined for the data-base points 34A, 34B, 34C. This relative positional information can be used to match spatial point 28A with data-base point 34A. While in FIG. 4 this distance and angle comparison is shown to be calculated for data-base points 34A, 34B and 34C, it is understood that the same relative positional information will be calculated for each combination of three points in image space comprising the currently considered data-base point 34A and two of its neighbours. Likewise, the same relative positional information will be calculated for the currently considered spatial point 28A, and two of its neighbours.

Figure 5:
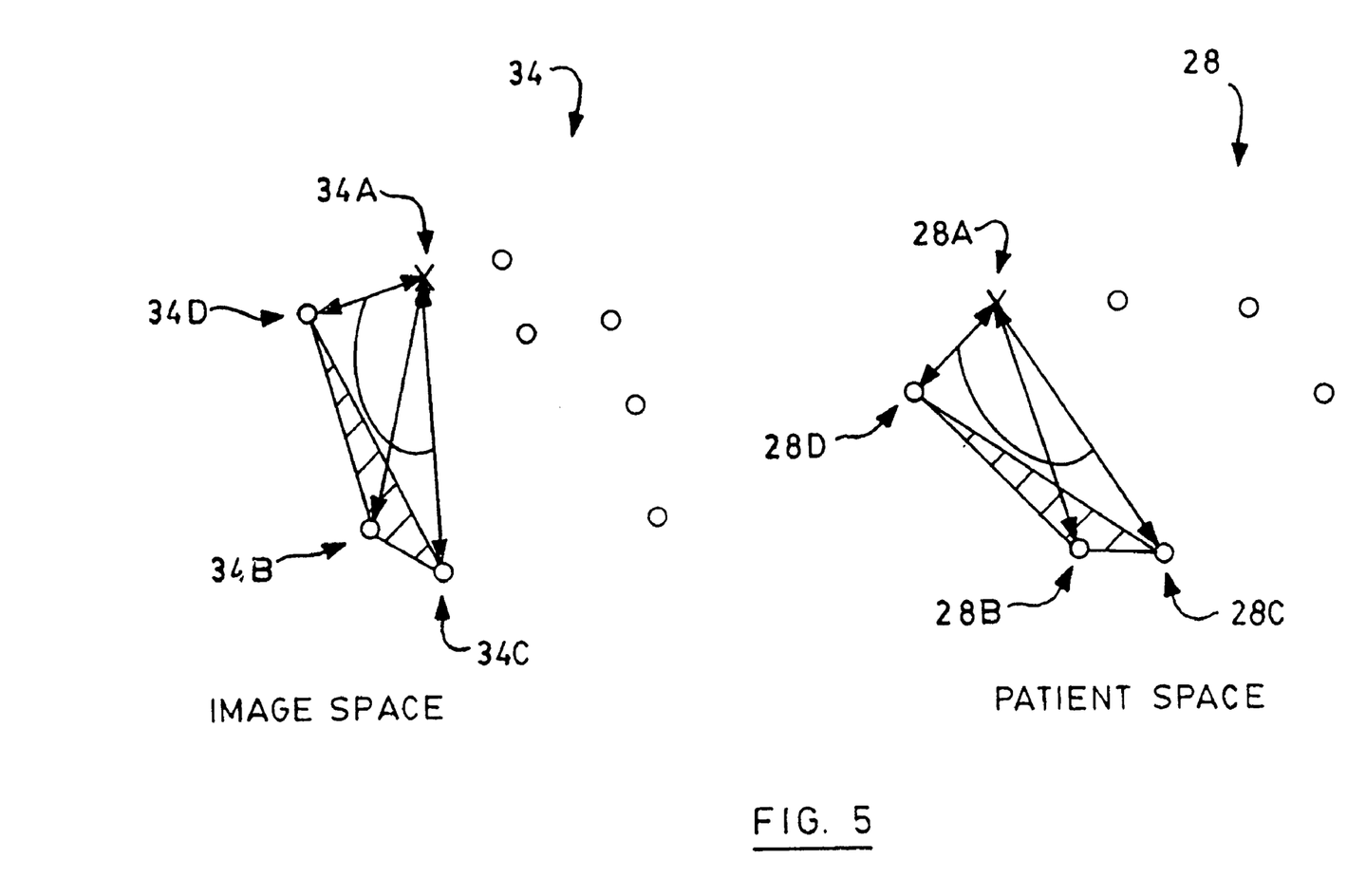
FIG. 5 shows a further embodiment of the present invention where tetrahedral volumes are used to match points.

Likewise, in addition to distance and angle information regarding groups of three points, relative positional information can be calculated for additional groups of points. For example, FIG. 5 illustrates the calculation of like signed tetrahedral volumes for groups of four data-base points 34A, 34B, 34C, 34D and groups of four spatial points in patient space 28A, 28B, 28C, 28D. As above, the tetrahedral volumes calculated for data-base points 34 in the image space will be compared to the tetrahedral volumes calculated for spatial points 28 in the patient space in order to determine if there is a match. In this case, groups of four points will be used in each space to validate each point, and, these calculations will be done for each group of four points in each space.

Figure 6:
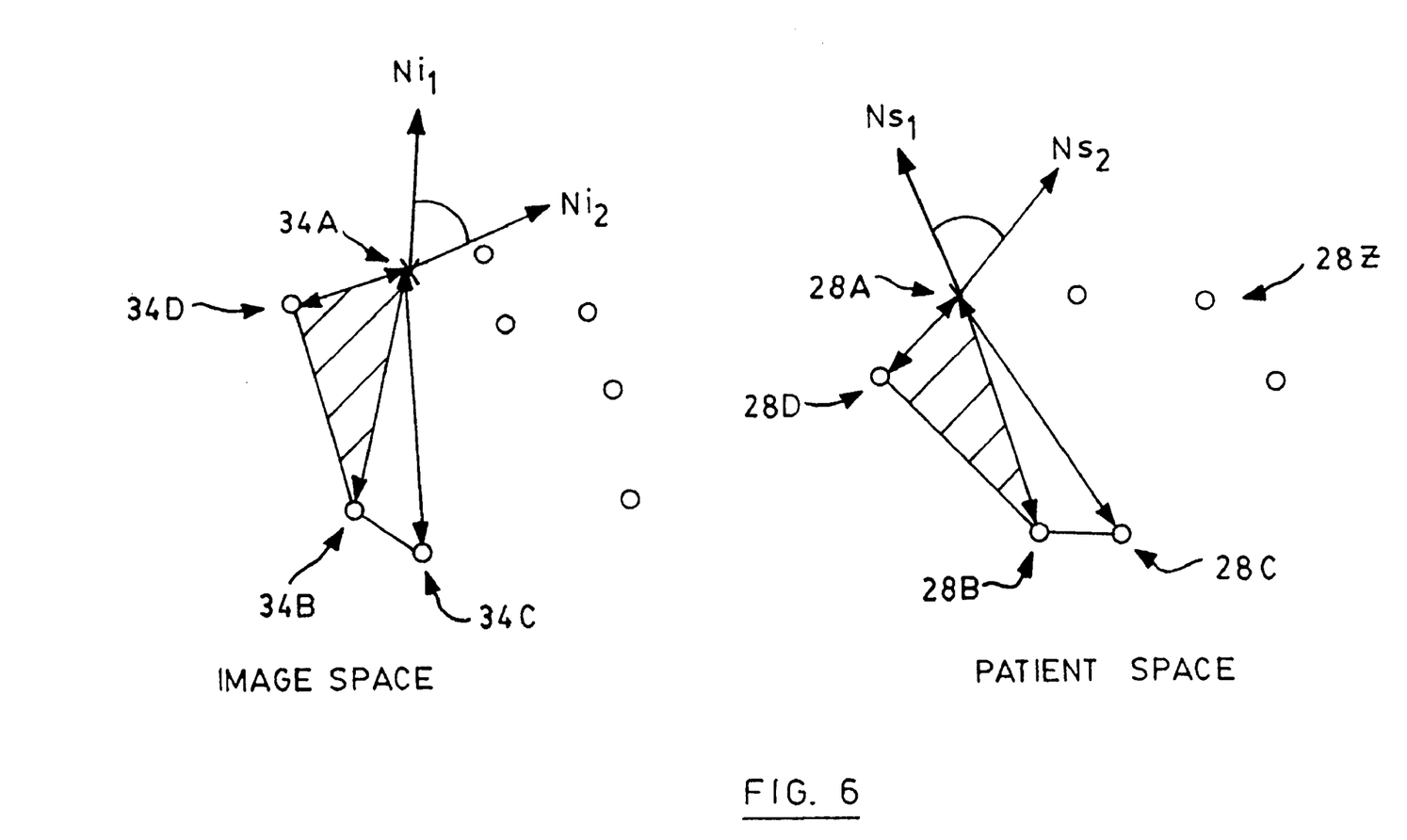
FIG. 6 shows a further embodiment of the present invention where angles between normals defined with respect to vectors from various points are used to match points.

Furthermore, as shown in FIG. 6, additional relative positional information regarding groups of points, such as normals defined with respect to vectors from various points, can be used to validate individual points. For example, as shown in FIG. 6, the angle between the image space normals $N_{i1}$ and $N_{i2}$ will correspond to the angle between the patient space normals $N_{s1}$ and $N_{s2}$ to validate a match between points 34A and 28A.

Accordingly, as a first indication of which data-base points 34 in the image space correspond to spatial points 28 in the patient space, relative positional information is determined between each of the spatial points 28 and likewise between each of the data-base points 34. Based on this relative positional information, the spatial points 28 will be matched to corresponding data-base points 34 by determining which of the spatial points 28 have relative positional information which correspond to the relative positional information between the data-base points 34.

It is understood that the number of image space points 34 may not be the same as the number of patient space points 28. Therefore, a match will occur when a majority of the minimum number of neighbouring points of either space have relative positional information which corresponds to the relative positional information in the other space. It is also apparent that not all spatial points 28 and data-base points 34 will find a corresponding match.

In addition, during the selection procedure, there is generally a tolerance with respect to the location of the points in each space. Therefore, the relative positional information must incorporate this tolerance and variances resulting from these tolerances.

It is understood that the above relative positional information which is calculated, as shown in FIGS. 3 to 6, are examples of the types of relative positional information which may be calculated to determine and validate matches between points in the image space and patient space. It is understood that the above relative positional information is not an exhaustive list of all of the different types of relative positional information which can be calculated.

However, regardless of the number of points in each space and the different types of relative positional information calculated for each point in each space, if the points are symmetrical about a plane or surface in each of the image space and patient space, there will always be a possibility that the points matched using the relative positional information are not in fact correct matches but rather symmetrical false matches. In general, purely relative positional information between the points in the image space and the patient space are insufficient to discriminate between a correctly matched point and the symmetrical false match. In order to make this discrimination, additional information, such as "global information" is needed.

In general, it is common for the patient 20 to have features which are symmetrical about a plane or surface, and for these symmetrical features to be manually selected by the surgeon. Therefore, by calculating the relative positional information and matching the points based on this information there will not be sufficient information to discriminate between the correct matches and the symmetrical false matches. A further test, namely a test to determine if a first matched spatial point 28A is a symmetrical false match of the corresponding data-base point 34A is needed.

For example, in FIGS. 3 to 6, the spatial point 28A would likely be matched with the data-base point 34A because the relative positional information calculated for each of these points with respect to their surrounding neighbours would be the same. In the case of the spatial point 28A and the data-base point 34A, the match is a correct match and not a symmetric false match as is apparent from the drawings. However, because the points in each of the patient space and image space is symmetrical, the relative positional information could have resulted in a match between point 28Z in FIG. 6 and point 34A. Point 28Z is the symmetrical false match for point 34A, because point 28Z is the mirror image of point 28A.

Figure 7:
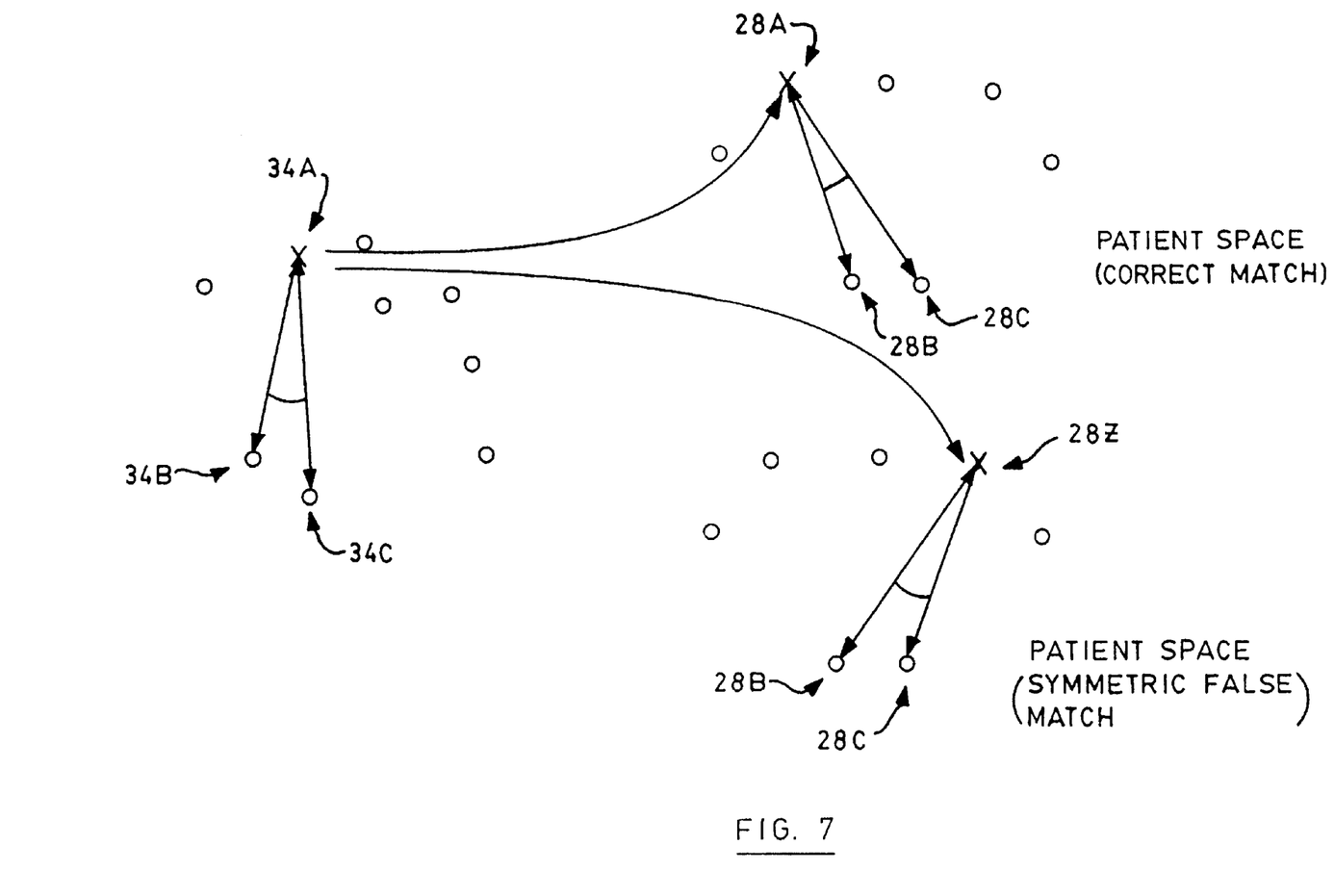
FIG. 7 shows a correct match and a symmetric false match between points in image space and spatial points in patient space.

This situation is illustrated in FIG. 7. FIG. 7 shows a matching of points in image space to points in the patient space based on distance and angle information, similar to the relative positional information shown in FIG. 4. However, FIG. 7 shows the correct match of spatial point 28A to data-base point 34A, as well as the symmetric false match of spatial point 28Z to data-base point 34A. It is apparent that this same situation could occur for any other symmetrical points.

FIG. 7 illustrates why relative positional information alone cannot be used to match data-base points 34 in the image space with spatial points 28 in the patient space when the points are symmetrical about a plane or surface, and the number of points in each space are not the same and/or the points have not been selected in any pre-determined order. In order to discriminate between the correctly matched points 34A and 28A, and the symmetric false match points 34A and 28Z, it is necessary to test for the symmetrical false match. One way to do so is by using the global information of all of the points in the image space and patient space.

In a preferred embodiment, this global information is determined by fitting the data-base points 34 to a first closed body 36 having a regular shape and a first surface 38 and likewise fitting the spatial points 28 to a second closed body 40 having the same shape as the first closed body 36 and a second surface 42. For example, reference is made to FIG. 8 which shows the points 28 in the patient space fitted to the second closed body 40. The second closed body 40 has a second surface shown generally in FIG. 8 by reference numeral 42. It is preferred to use all of the points 28, 34 in each space when forming a closed body 36 or 40, but, in general, at least four points are needed for a closed body to be fitted.

Figure 8:
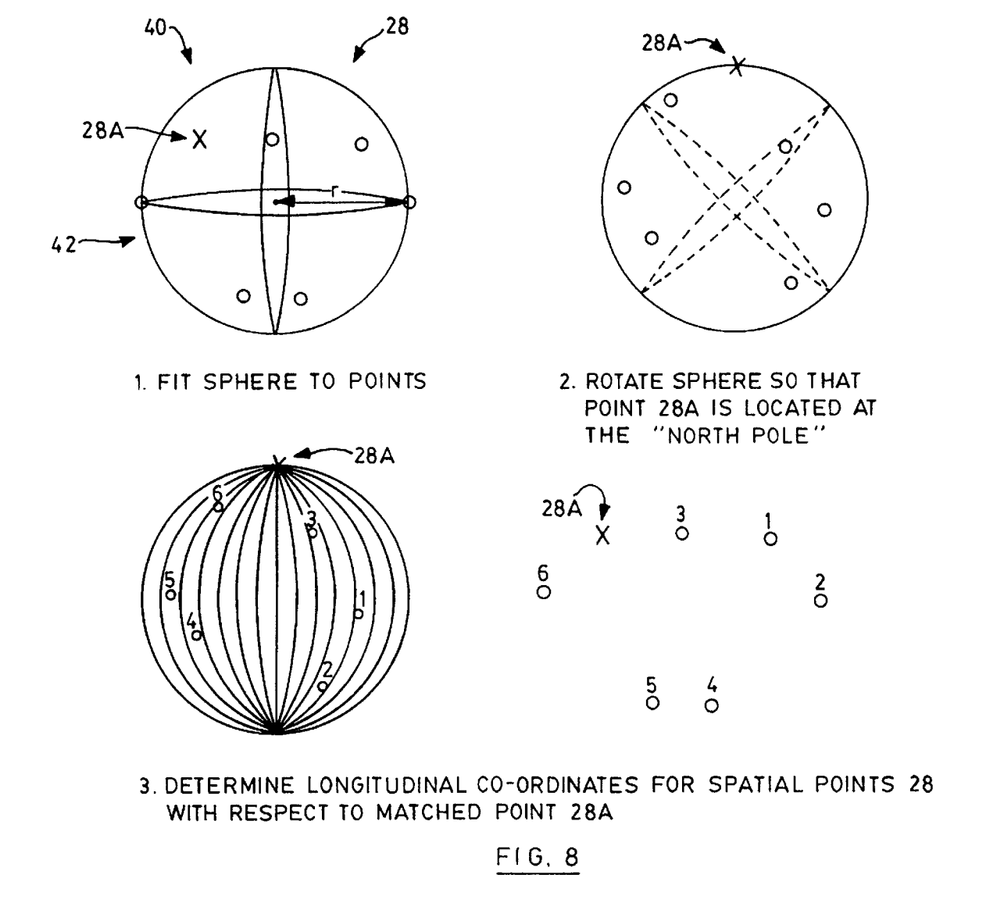
FIG. 8 shows spatial points being fitted to a sphere and the longitudinal coordinates being calculated.

In a preferred embodiment, as shown in FIG. 8, the second closed body 40 is spherical. While any closed body could be used, a sphere is preferred because the calculations are simpler and easier to perform. In another embodiment, the second closed body is an ellipsoid (not shown), which would generally provide a better fit for points 28 distributed on a patient's face, but the calculations would be more difficult. It is preferable that the closed body 40 have a regular shape, meaning that the body 40 is symmetrical or defined by a mathematical equation so that the fitting and the following calculations can be easily performed.

In a similar manner, the corresponding data-base points 34 are fitted to a first closed body 36 (shown in FIG. 9) having a regular shape and a first surface 38. The shape of the first closed body 36 and the second closed body 40 are the same, which in this embodiment is a sphere.

Figure 9:
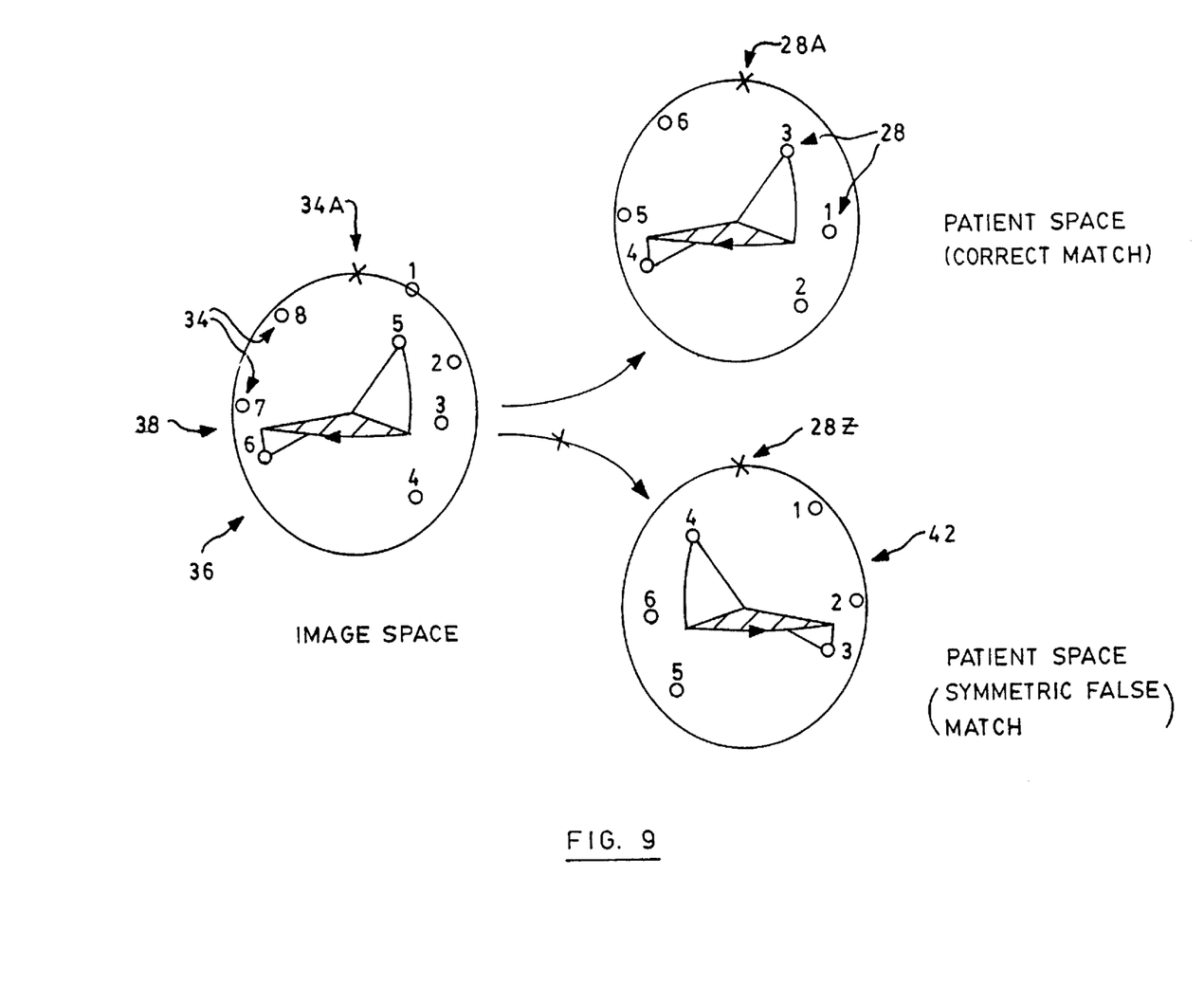
FIG. 9 shows the determination of a correct match and a symmetric false match according to one embodiment of the present invention.

As shown in FIG. 9, once the spatial points 28 are fitted to the second closed body 40 the points 28 are projected onto the second surface 42. The points 28 are projected onto the second surface 42 because generally not all of the points will fit exactly through the second closed body 40. In a similar manner, the data-base points 34 will be projected onto the first surface 38 of the first closed body 36. In addition, as shown in FIGS. 8 and 9, the spatial points 28 are projected onto the second surface 42 in a particular orientation, and, likewise, the data-base points 34 will be projected onto the first surface 38 in a particular orientation.

The orientation of the spatial points 28 with respect to the currently considered point 28A on the second surface 42 will then be compared to the orientation of the data-base points 34 with respect to the corresponding data-base point 34A on the first surface 36. If the orientation of the spatial points 28 corresponds to the orientation of the data-base points 34, then point 28A is correctly matched to data-base point 34A. However, if the orientations do not correspond, then the match is not validated because the spatial point 28 is a symmetric false match of the corresponding data-base point 34.

In a preferred embodiment, as shown in FIGS. 8 and 9, the orientation of the spatial point 28A is compared with respect to the other or neighbouring spatial points 28 by rotating the second spherical closed body 40 such that the matched spatial point 28A is at the top or "north pole" of the closed body 40. At this position, the surface 42 of the second closed body 40 can be sectioned with lines resembling lines of longitude. Longitudinal coordinates of the neighbouring spatial points 28 can then be calculated with respect to the longitudinal lines passing through the currently considered spatial point 28A. It is understood that the step of rotating the sphere such that the currently considered spatial point 28A is aligned with the "north pole" is done simply to illustrate the principle, and longitudinal coordinates for the neighbouring points 28 with respect to the spatial point 28A could be calculated without rotation of the second closed body 40.

Likewise, a similar fitting and comparison of the orientation of the data-base points 34 with respect to the corresponding data-base point 34A can be made. In a preferred embodiment, the comparison of the data-base points 34 is performed by determining longitudinal coordinates of each of the data-base points 34 with respect to the data-base point 34A corresponding to spatial point 28A.

FIG. 9 shows the first closed body 36 and the data-base points 34 projected thereon. As illustrated by FIG. 9, when a comparison is made of the orientation of the neighbouring spatial points 28 in the patient space with respect to the correct match, namely spatial point 28A, the orientation of the neighbouring spatial points 28 on the second surface 42 corresponds to the orientation of the data-base points 34 with respect to the corresponding data-base point 34A on the first surface 38. In the preferred embodiment, where the orientation is compared by means of calculating longitudinal coordinates with respect to the currently considered spatial point 28A and the currently considered data-base point 34A, the difference between the longitudinal coordinates of neighbouring data-base points 34 in the image space should correspond to the differences between the longitudinal coordinates of neighbouring spatial point 28 in the patient space, if the points 28A and 34A are correctly matched. For example, the longitudinal difference from points 3 to 4 of the neighbouring spatial points 28 is the same as the longitudinal difference of points 5 to 6 of the data-base points 34. By contrast, when the longitudinal differences are compared for the symmetric false match, namely spatial point 28Z, the longitudinal difference from points 3 to 4 is directly opposite to the longitudinal difference for corresponding data-base points 5 and 6. In this way, the symmetric false match 28Z and the correct match 28A will be determined.

The difference between the longitudinal differences can be fairly large and still constitute a correct match. The reason for this is that the points between the image space and the patient space may cause differences in fitting of the first closed body 36 and the second closed body 40. Furthermore, in order to discount clearly erroneous points in either the image space or patient space, a voting system may be instigated wherein the correctness of different points is determined by the number of correct votes or correct matches. In any event, a large tolerance is usually acceptable for the longitudinal differences, such that a correct match will be determined if the longitudinal differences are less than 25 degrees apart.

In the event that the matched spatial point is determined to be the symmetric false match, namely point 28Z, of the corresponding data-base point 34A, then the matching step can be repeated in order to attempt to locate another match. For example, if in the original matching procedure data-base point 34A was matched with data-base point 28Z, and it was determined that spatial point 28Z was the symmetric false match for data-base 34A, the matching step will be repeated. If another matching procedure is performed using relative positional information, but point 28Z is excluded from consideration, it is much more likely that data-base point 34A will be matched with spatial point 28A. The test to determine if the matched spatial point 28A is the symmetric false match of the corresponding data-base point 34A will then determine that they are not symmetric false matches but correct matches.

The same procedure will be repeated for each of the other spatial point 28 and each of the other data-base points 34. For example, each spatial point 28 will be considered in turn and the orientation, such as the longitudinal co-ordinates, of the neighbouring spatial points 28 will be determined with respect to the point being considered. Likewise, each data-base point 34 will be successively considered.

In general, once the spatial points 28 have been fitted to the second closed body 40 and the spatial points 28 have been projected thereon, the same closed body 40 can be used when each of the spatial points 28 are considered, and the fitting process need not be repeated. This is also the case with the first closed body 36 to which the data-base points 34 have been fitted.

After all of the spatial points 28 and data-base points 34 have been considered, and the corresponding points 28, 34 have been matched, a mapping transformation will be determined. It is possible that not all of spatial points 28 will be matched to a data-base point 34. In fact, if there is a different number of data-base points 34 than spatial points 28, it is inevitable that not all spatial points 28 will match with a corresponding data-base point 34.

Once at least three, and preferably more, spatial points 28 have been matched with corresponding data-base points 34, the computer 14 will have sufficient points to determine the mapping transformation from the image space to the patient space. The computer 14 will then calculate the mapping transformation completing the registration procedure. In the event all the points 28, 34 have been considered and at least three spatial points 28 have not been matched with corresponding data-base points 34, the user of the system 10 will be requested to repeat the step of selecting spatial points 28 and/or data-base points 34. In other words, the system 10 will ask that more points be selected in either patient space, image space or both. This will be repeated until at least three spatial points 28 are matched to corresponding data-base points 34 and the matches are not symmetrical false matches of the corresponding data-base points 34.

It is clear that the best results can be obtained if the data-base points 34 and the patient space points 28 can be stably fitted to a sphere or other closed body. In order to ensure that the best fit can be made, when selecting the data-base points 34 and the patient space points 28, it is preferable to test the data-base points 34 and the spatial points 28 to determine if they are coplanar or nearly coplanar. If the data-base points 34 are coplanar or nearly coplanar, it will be preferable to select additional data-base points 34 on the data-base body 32 such that they are no longer coplanar or nearly coplanar. A similar situation will arise if the selected spatial points 28 are coplanar or nearly coplanar.

In order to better determine the mapping transformation, it is preferable to minimize errors between each spatial point 28 and the corresponding value obtained in image space by the registration procedure by using a root-mean-square analysis. In some cases, it is possible that an incorrect match has occurred. In this case, it is necessary to exclude the faulty data or faulty point from the registration procedure.

This can be done in one of two ways. First, the individual fitting error for each point is computed using root-mean-square analysis. If the fitting error for one particular point is exceptionally large and beyond a pre-determined threshold value, that point can be excluded from the points used to determine the mapping transformation.

Second, it is possible that an outlying point corrupts the root-mean-square analysis. In this case, it is necessary to iteratively retry the root-mean-square analysis with combinations of points disabled, to determine the smallest overall fitting error. Because this iteration is computationally expensive, it is done sparingly, for example when the overall fitting error is greater than a pre-determined threshold value, suggesting that an outlying point has corrupted the registration procedure. When the overall fitting error is small, and less than the pre-determined threshold value, the first method of excluding faulty data will be performed.

The system 10 shown in FIG. 1 can be used to perform the process described above to correlate spatial points 28 on the patient 20 with data-base points 34 on the data-base body 32. The probe 12 can be used to select the at least four spatial points 28 on the patient 20 which will be matched with the data-base points 34. As stated above, the spatial points 28 selected on the patient 20 can correspond to distinctive features on the face of the patient 20, and/or markers placed on the patient 20. Once the probe is placed on a marker or feature of the patient 20, the spatial position of the spatial point 28 in patient space will be determined by the spatial determinator 25 and entered to the computer 14 thereby selecting the spatial point 28.

As stated above, the data-base body 32 is based on previously acquired images 22 stored in the data storage unit 16. The data-base points 34 are selected on the data-base body 32 by means of a data-base point selector 108 shown in FIG. 10. The data-base point selector simply identifies points on the data-base body 32 in image space and determines the data-base position of the data-base points 34 with respect to the image origin 30.

Figure 10:
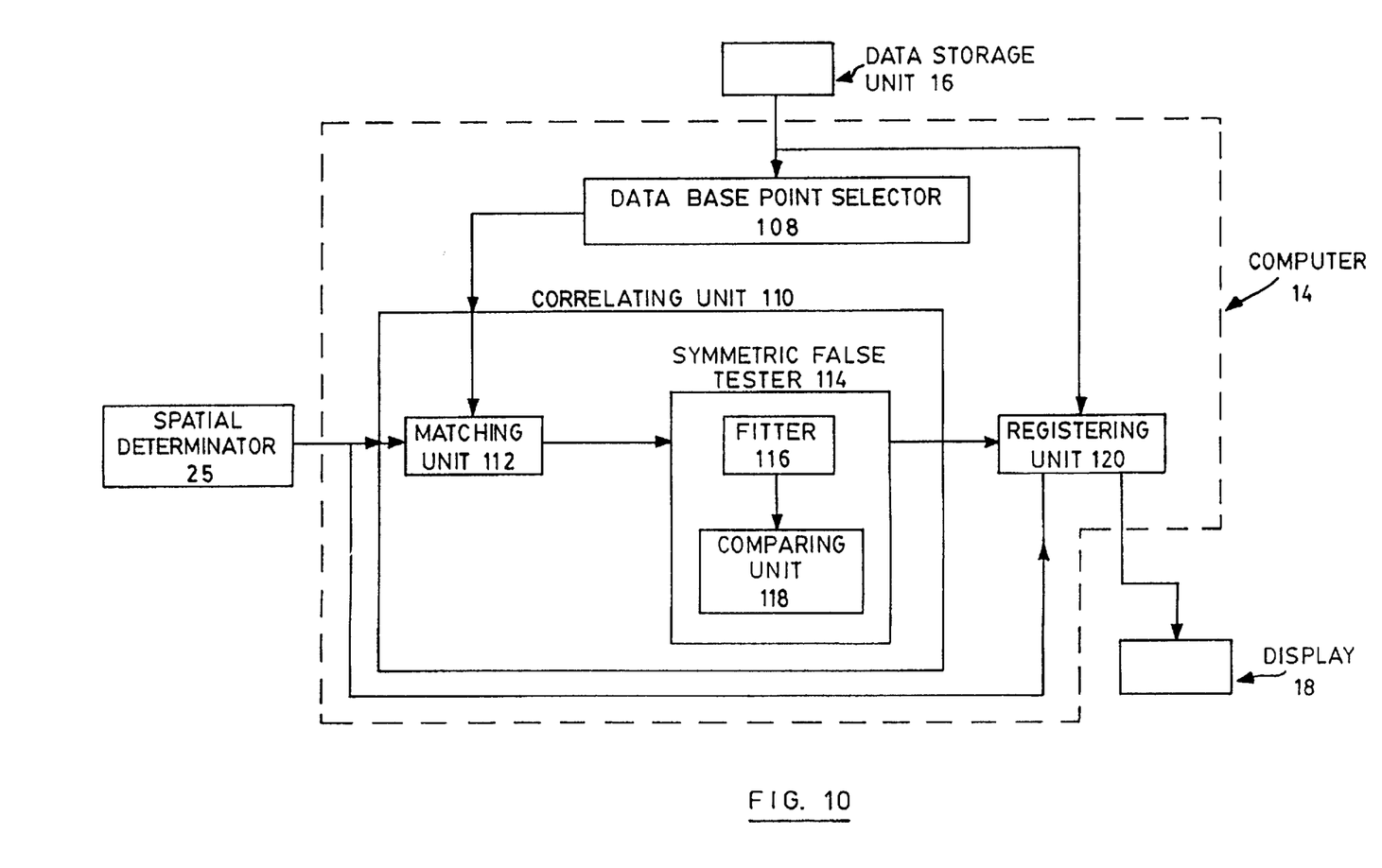
FIG. 10 shows a block diagram representing a further embodiment of the present invention.

FIG. 10 is a block diagram showing the various components and functions performed by the computer 14. It is understood that the computer 14 can be a single computer, a combination of different computer elements, and a remotely located processing unit In addition, it is understood that the functions and units identified as forming part of the computer 14 could be hardware or software driven.

As shown in FIG. 10, the spatial position of the spatial points 28 and the data-base position of the data-base points 34 are received by the correlating unit 110. The correlating unit 110 correlates the spatial points 28 with the data-base points 34.

The correlating unit 110 comprises a matching unit 112. The correlating unit 110 sends the spatial position of the spatial points 28 and the data-base position of the data-base points 34 to the matching unit 112. The matching unit then attempts to match the spatial points 28 with the data-base points 34. The matching unit 112 does this by determining the relative positional information between the data-base points 34 and the positional information between the spatial points 28, as described above, and as shown for example in FIGS. 3 to 6. Various combinations of relative positional information could be used to attempt to match the spatial points 28 with the data-base points 34, and, the relative positional information described above and shown in FIGS. 3 to 6 are a non-exhaustive examples of such relative positional information.

After computing the relative positional information for the spatial points 28 and the data-base points 34, the matching unit 112 will match a spatial point 28 with a corresponding data-base point 34 if the relative positional information of the spatial point 28 corresponds to the relative positional information of the corresponding data-base point 34. The relative positional information will be considered to correspond if the relative positional information for a majority of the neighbouring points in each space is below a pre-determined threshold value.

Once this has been determined for all or most of the spatial points 28 and data-base points 34, the matching unit 112 sends this information to the symmetric false tester 114. The symmetric false tester 114 tests the matched spatial points 28 to determine if one or more of the matched spatial points 28 are symmetric false matches of the corresponding data-base points 34 using the procedure described above.

The symmetric false tester 114 comprises a fitter 116. The fitter fits at least four and preferably all of the data-base points 34 to a first closed body 36 having a regular shape and first surface 38, such that the data-base points 34 are projected onto the first surface 38 in a first orientation as described above and shown in FIGS. 8 and 9. Preferably, the first closed body 36 is spherical so that the calculations are easier to perform. The fitter 116 also fits the spatial points 28 to a second closed body 40 having the same shape 42 as the first closed body 36. The second body 40 also has a second surface 42 and the spatial points 28 are projected onto the second surface 42 in a second orientation. The orientation of the spatial points 28 on the second surface 42 is then compared to the orientation of the data-base points 34 on the first surface 38 by the comparing unit 118.

The comparing unit 118 compares the orientation of the spatial points with respect to each one of the matched spatial points 28 on the second surface 42 to the orientation of the data-base points 34 with respect to the corresponding data-base point 34 on the first surface 38 as described above and shown in FIG. 9. In the preferred embodiment, the comparing unit 118 calculates longitudinal co-ordinates of the neighbouring points for each of the spatial points 28 and data-base points 34 which are being considered. The longitudinal difference between any two neighbouring spatial points 28 will then be determined and compared to the longitudinal difference of groups of two neighbouring data-base points 34 as described above and shown in FIGS. 8 and 9. A match of a spatial point 28A to a corresponding data-base point 34A will be considered a correct match and not a symmetric false match of the corresponding data-base point 34A if the orientation of the neighbouring spatial points 28 on the second surface 42 corresponds to the orientation of the neighbouring data-base points 34 on the first surface 38. The spatial point 28Z will be considered a symmetric false match of the corresponding data-base point 34A if the differences in longitude between the neighbouring spatial points 28 do not correspond to the differences in longitude between the neighbouring data-base points 34. The differences in longitude will correspond if they are less than a predetermined threshold, such as 25 degrees. This test will be performed for each pair of matched points to validate the match as not being a symmetric false match. Should a match be found to be a symmetric false match, the comparing unit 118 will ask the matching unit 112 to exclude the symmetric false match and determine new matches.

The symmetric false tester 114 will send the spatial positions of all of the matched spatial points 28 and the data-base position of the corresponding data-base points 34 which have been found not to be symmetric false matches to the registering unit 120. The registering unit 120 will then use the spatial position of the spatial points 28 and the data-base position of a corresponding data-base points 34 to register the patient 20 to the data-base body 32. The registration procedure will essentially take the form of calculating a transformation mapping of the patient 20 to the data-base body 32.

Once the registering unit 120 has registered the patient 20 to the data-base body 32, the display means 18 can display the portion of the data-base body 32 corresponding to the region of the patient 20 which the probe 12 is near. The display 18 can do this by transforming the position of the probe 12 onto the data-base body 32 using the transformation mapping calculated by the registering unit 120.

Figure 11:
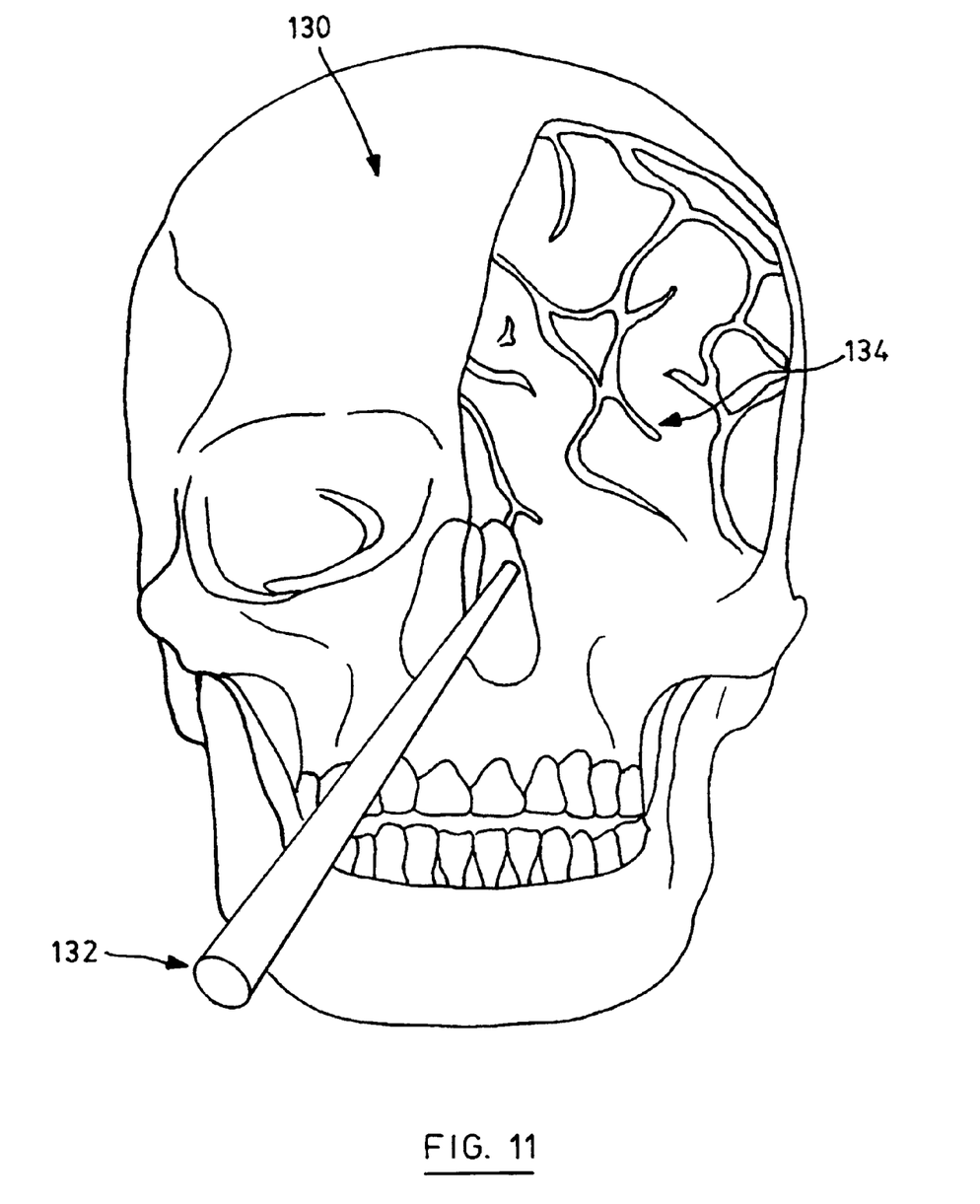
FIG. 11 shows a display format resulting from the system of FIGS. 1 and 10.

The data-base body 32 may be presented in different formats. For example, a three-dimensional model 130 of the patient 20 may be generated by the computer 14 from the images 22 as shown in FIG. 11. The computer 14 could also generate a three-dimensional representation 132 of the probe 12. The three-dimensional representation 130 of the patient 20 generated from the stored images 22 is presented together with the representation 130 of the probe 12 on the display 18. The relative locations of the representation 132 of the probe in image space on the display 18 will correspond to the spatial position and orientation of the probe 12 relative to the patient 20, as determined by the spatial determinator 25. This is done by transforming the spatial position of the probe 12 as determined by the spatial determinator 25 to the image space using the transformation mapping calculated by the registering unit 120.

FIG. 11 shows the position and orientation of the three dimensional representation 132 of the probe 12 on the three dimensional representation 130 of the data-base body 32 where a wedge shaped cut-out portion 134 has been removed from the three dimensional representation 130 of the data-base body 32. This allows the display and viewing of regions of the patient 20 in relation to the probe 12 which can not be seen from viewing the patient 20. Other viewing options are available as is known in the art.

In the event that the correlating unit 110 does not correlate at least three spatial points 28 to corresponding data-base points 34, such that three spatial points 28 are matched with corresponding data-base points 34 and the matches are not determined to be symmetric false matches, then system 10 will the user select additional data-base points 34 and/or additional spatial points 28. This will continue until at least three pairs of points have been correlated so that the registration procedure can be completed. It is understood that when a user is selecting spatial points 28 and data-base points 34, the user will attempt to select points 28, 34 which can be matched. So that in general, it will not be necessary to repeatedly request the user to select additional points 28, 34.

While reference has been made to the facial features and head of the patient 20, it is understood that the present process and system 10 can be used in association with any other anatomical feature of the patient 20, such as the vertebrae. In addition, while the process and system 10 had been described with respect to a patient 20 and the anatomical features or body of the patient 20, it is understood that the invention is not restricted to anatomical bodies. Rather, the present system and process can be used to correlate points on any spatial body to points on a data-base body formed from pre-acquired images of the spatial body.

It is understood that the calculations which form part of this procedure can be performed in any order. In particular, a spatial point 28A in patient space can be considered and matched to a data-base point 34A in image space by determining relative positional information between these points 28A, 34A and their neighbours. At the time, it can be determined whether or not the points 28A, 34A are a symmetric false match by fitting the points 28, 34 to a closed body and comparing the orientation of the neighbours. Alternatively, each spatial point 28 can be considered successively and all relative position information, as well as all orientation information from fitting the points 28 to a closed body, can be determined for all of the spatial points 28 at once. In a similar manner, each of the data-base points 34 can be successively considered. Once all of this information has been calculated, points 28, 34 are matched and the matches are validated based on the orientation information previously determined. These are examples of the order the steps in the procedure can be executed.

It will be understood that, although various features of the invention have been described with respect to one or another of the embodiments of the invention, the various features and embodiments of the invention may be combined or used in conjunction with other features and embodiments of the invention as described and illustrated herein.

Although this disclosure has described and illustrated certain preferred embodiments of the invention, it is to be understood that the invention is not restricted to these particular embodiments. Rather, the invention includes all embodiments which are functional, mechanical or electrical equivalents of the specific embodiments and features that have been described and illustrated herein.

The embodiments of the invention in which an exclusive property or privilege is claimed are defined as follows:

1. A method for automatically correlating a plurality of spatial points on a spatial body to corresponding plurality of data points on a database body, comprising the steps of:

(a) selecting a group of spatial points and for each spatial point determining the relative position between the selected point and the remaining spatial points in the group;

(b) selecting a group of data points, and for each data point determining the relative position between the selected data point and the remaining data points; and (c) comparing the spatial relationship for each data point and each spatial point using the relative position information to determine a match between the spatial and data points to thereby correlate the spatial points with the data points.

2. A method as defined in claim 1, said methods including testing a matched spatial point for determining whether it is a desired spatial point or an undesired symmetric spatial point.

3. A method as defined in claim 1, including the steps of detecting and discarding symmetric false matches by fitting the spatial points and database points to a first and second closed body, respectively.

4. A method as defined in claim 3, including the step of comparing the orientation of the spatial points and of the database points projected on the closed bodies.

5. A method for independently correlating a plurality of spatial points on a spatial body to corresponding plurality of data points on a database body comprising the steps of:

(a) projection of at least four data points, including a reference point, on to a first surface and a first orientation;

(b) projection of at least four data points, including a second reference point on to a second surface and a second orientation;

(c) comparing the orientation of the spatial points and database points; and (d) deriving a match signal.

* * * * *